United States Patent [19]

Illner

[11] Patent Number: 5,709,672
[45] Date of Patent: Jan. 20, 1998

[54] SILASTIC AND POLYMER-BASED CATHETERS WITH IMPROVED ANTIMICROBIAL/ANTIFUNGAL PROPERTIES

[75] Inventor: Hana Illner, Lubbock, Tex.

[73] Assignee: Texas Tech University Health Sciences Center, Lubbock, Tex.

[21] Appl. No.: 551,544

[22] Filed: Nov. 1, 1995

[51] Int. Cl.$^6$ .................................................. A61M 25/00
[52] U.S. Cl. ............................................. 604/265; 2/161.7
[58] Field of Search ........................... 2/161.7; 604/265; 424/404, 423, 430; 427/2.3

[56] References Cited

U.S. PATENT DOCUMENTS

| | | | |
|---|---|---|---|
| 4,473,585 | 9/1984 | Abrahamsson et al. | 424/318 |
| 4,592,920 | 6/1986 | Murtfeldt | 427/2 |
| 4,642,104 | 2/1987 | Sakamoto et al. | 604/265 |
| 4,675,327 | 6/1987 | Fredrick | 514/383 |
| 5,019,096 | 5/1991 | Fox, Jr. et al. | 427/2.25 |
| 5,120,325 | 6/1992 | Dow, Jr. | 604/304 |
| 5,128,168 | 7/1992 | Shlenker et al. | 427/2.3 |
| 5,130,159 | 7/1992 | Shlenker et al. | 427/2.3 |
| 5,165,953 | 11/1992 | Shlenker et al. | 427/2.3 |
| 5,281,662 | 1/1994 | Ito et al. | 525/54.1 |
| 5,395,651 | 3/1995 | Sodervall et al. | 427/305 |
| 5,409,463 | 4/1995 | Thomas et al. | 604/167 |

FOREIGN PATENT DOCUMENTS

0 206 024  12/1986  European Pat. Off. .

OTHER PUBLICATIONS

Bhatnagar, V. et al., "Studies on antibacterial properties of gentian violet impregnated silastic," (Abstract only) *Indian J Med Res*, vol. 97, pp. 206–208 Sep. (1993).

Docampo, et al., "The Metabolism and Mode of Action of Gentian Violet," *Drug Metabolism Reviews*, 22(2&3), 161–178 (1990). No month available.

Illner, et al., "Use of Topical Antiseptic in Prophylaxis of Catheter–Related Septic Complications," *Surgery, Gynecology & Obstetrics*, Jun. 1989, vol. 168, pp. 481–490.

"Prevention of Catheter–Associated Urinary–Tract Infections by use of Silver–Impregnated Catheters," Letters to the Editor, *The Lancet*, Nov. 1, 1986, p. 1031.

Beam, Jr., et al., "Preventing Central Venous Catheter–Related Complications," *Infections in Surgery*, pp. 1–13, Oct. 1990.

Maki, et al., "An Attachable Silver–Impregnated Cuff for Prevention of Infection with Central Venous Catheters: A Prospective Randomized Multicenter Trial," *The American Journal of Medicine*, vol. 85, pp. 307–314, Sep. 1988.

Maki, et al., "Study Results of the Vitacuff© Infection Control Device Including the Abstract Entitled: Multicenter Trial of an Attachable Silver–Impregnated Subcutaneous Cuff for Prevention of Infection with Central Venous Catheters," Twenty–Seventh Interscience Conference on Antimicrobial Agents and Chemotherapy, New York, New York, Oct. 5, 1987.

Abstract, *American Journal of Infection Control*, p. 79, vol. 16, No. 2, Apr. 1988.

Schaeffer, et al., "Effect of Silver Oxide/Trichloroisocyanuric Acid Antimicrobial Urinary Drainage System on Catheter–Associated Bacteriuria", *The Journal of Urology*, vol. 139, pp. 69–73, Jan. 1988.

*Primary Examiner*—Diana Dudash
*Attorney, Agent, or Firm*—Denise Mayfield

[57] ABSTRACT

Disclosed are devices having improved anti-microbial resistance to bacteria and fungus. Indwelling devices, such as catheters and the like, include low amounts of gentian violet, or a combination of gentian violet and silver nitrate. Methods for preparing the treated devices using alcohol and similar solvents are also detailed. The devices may be made of polyurethane, silicone, or other similarly absorptive material. Methods of inhibiting infection and long-term catheter management with the described devices are also disclosed.

10 Claims, 4 Drawing Sheets

SILASTIC AND POLYMER-BASED CATHETERS WITH IMPROVED ANTIMICROBIAL/ANTIFUNGAL PROPERTIES

BACKGROUND OF THE INVENTION

1. Field of the Invention

The present invention relates generally to the field of indwelling medical articles, such as catheters. These articles are coated or otherwise treated with gentian violet, a combination of gentian violet and silver nitrate, or like combination of bacteriostatic and antifungal chemical derivatives at relatively low concentrations, that imparts effective microbial resistance to the device. The devices of the invention have at least one surface that is of a silastic, polyurethane, or like absorptive and/or semiabsorptive material. The invention also relates to highly efficient methods or preparing these articles. Methods of using the treated articles for inhibiting infection, especially during long-term catheterization, are also related to the present invention.

2. Description of the Related Art

Catheters pre-treated with antibiotics have been used experimentally in the past for prophylaxis of septic complications. At present, their use remains controversial because of their short-term potency and because of the risks associated with overgrowth of resistant bacterial strains and fungal superinfection.

The introduction of plastic catheters in 1945 allowed prolonged administration of intravenous fluids through single sites. The subsequent use of central venous catheters for long term intravenous therapy and for continuous cardiovascular monitoring has also been described. However, these and other common catheter uses have been associated with a number of serious complications, including formation of thrombus, bacterial and fungal colonization, bacteremia, systemic sepsis and shock.

Clinical sepsis, accompanied by positive catheter tip and blood cultures with the same organism, are the most feared of complications, and remain the primary reasons for catheter removal. This often occurs at a time when central venous access is crucial for infusion and monitoring. Removal of the infected catheter, with or without the addition of systemic antibiotics, is successful in resolving some of these complications. The removal of an infected catheter or the routine use of systemic antibiotics for prophylaxis of catheter sepsis for that matter, however, does not resolve the problem of antibiotic and other resistant bacterial strains and fungal superinfection. This is a particularly troublesome problem in chronically ill or immunologically compromised patients, as this population frequently are in need of long term catheterization. Most notable among this group are burn patients and patients infected with AIDS, who suffer three times the frequency of Candida and an increased rate of Staphylococcus aureus infections.[37,38]

Topical prophylaxis of septic complications using antibiotics has been used to control/inhibit infection. Catheter antibiotic pretreatment has also been used in an attempt to reduce catheter colonization. However, this approach typically provides limited infection control; only a small fraction of the bound antibiotics being found to remain 48 hours after insertion of a device with antibiotic treatment. The relatively limited effective shelf-life of antibiotics is an additional undesirable limitation associated with this approach. More effective and lasting agents with a longer shelf-life are desirable, considering the delayed onset of septic complications and the high percentage of reported fungal infections.

Catheters for patient care that are treated to include metal antimicrobial compounds, such as silver and silver oxide, have also been described. For example, U.S. Pat. No. 4,592,920 (Baxter-Travenol)[1] relates to a method for producing an antimicrobial catheter having an antimicrobial metal compound. The anti-microbial metal compound is first prepared in a suspending agent (for example, silicone, polyurethane, or tetrafluoroethylene) and used to fabricate the catheter or to coat a catheter. Examples of these antimicrobial metal compounds are silver, silver oxide, gold thiogylclate and copper oxide. European patent application No. 0206024 (Becton Dickinson),[2] also relates to the antimicrobial effects of silver.

Silver nitrate pretreatment of silastic catheters (using a silver nitrate in alcohol technique) has previously been reported by the present inventors to impart E. coli resistance to a treated surface.[3] Silver nitrate suspended in alcohol has also been observed to provide a more effective and rapid impregnation of silastic than silver nitrate in water (Id.). Silver sulfadiazine with chlorhexidine and other sulfa drugs have also been used with commercial catheters to enhance infection resistance. For example, the Arrow antiseptic catheter (Arrow Gard Blue™) is a molded polyurethane device that includes the above combinations of silver and/or chlorhexidine compounds. These catheters have been reported to have antimicrobial activity against Escherichia coli, Pseudomonas aerugeinosa, Staph. epidermidis, Staphaureus, Candida albicans and Klebsiella pneumoniae[18]. However, lesser activity against Candida and Staphylococcus aureus has been observed, rendering them less useful for controlling infection in long-term, immunologically suppressed and chronically catheterized patients; Staphylococcus aureus was reported in 73% of reported bacterimias in AIDs patients,[20] and Candida albicans was the prevalent organism in 12% of colonized catheters of patients with burns[21]. The acquired bacterial resistance to silver ions reported in burns[16] may also lower the effectiveness of these antiseptic catheters in preventing catheter-related infections.

Relatively high concentrations of gentian violet have been used as an antiseptic, as well as for controlling infection. Docampo (1990)[7] provides a general textbook description of the metabolism and mode of action of gentian violet, and its use as an antiseptic at concentrations from 1–2% (10–20 mg/ml) in aqueous solution. A highly variable and concentration-dependent anti-Staphylococcal epidermidis activity with GV has been observed in studies with this compound on silastic discs at concentrations of from 1% to 5%. Reduced anti-Staph activity was also reportedly observed with a 1% GV concentration, compared to the 2% treatments. Significant differences were not observed between the 2% and 5% concentrations. Gentian violet has also been described for local application (in a 0.5–2.0% aqueous solution) in the treatment of thrush[8,11], as an antihelmenthic agent, for intravascular administration (0.04% solution), and as an additive in whole blood transfusion to prevent Chagas disease.[10] However, the safety of using these relatively high concentrations of gentian violet,[5,11] and the potential carcinogenic activity of the agent,[6] have discouraged widespread use. Gentian violet also has a characteristic purple color that, when used at the relatively high concentrations discussed in the art[4], causes an undesirable "tattooing" or staining effect on tissues[7].

A need continues to exist in the art for devices, particularly for in-dwelling medical devices, that provide effective long-term infection control. Improved techniques for preparing such devices, preferably with less expensive, stable, slow-releasing bacteriostatic materials, would provide a desirable alternative to antibiotic and metal-treated devices.

It is an object of the invention to provide bacteriostatic and anti-fungal medical devices that are suitable for long-term infection control. It is a further object of the invention to introduce unique indwelling device treatments that provide effective infection control using anti-microbial agents that do not give rise to antibiotic-resistant microbial strains.

SUMMARY OF THE INVENTION

The present invention demonstrates that low amounts of gentian violet, or a combination of gentian violet and silver nitrate, provides for an improved and microbially resistant device using anti-microbial agents that do not give rise to antibiotic resistant microbial strains. The present invention, in a general and overall sense, concerns medical devices of silicone or polyurethane, and like materials that include relatively low concentrations of gentian violet or mixtures of gentian violet and silver nitrate. These devices are found by the present inventors to have extraordinarily effective antibacterial and antifungal activity. These elegantly simple devices provide amazingly effective antimicrobial activity at concentrations several fold lower than gentian violet concentrations previously contemplated in the literature. Potential undesirable characteristics associated with "tattooing" or discoloration of tissues are thus reduced, without loss of bacteriostatic activity. Other advantages of the invention include improved, longer term protection against infection of both bacterial and fungal origin. Such is accomplished without antibiotics, thus reducing the incidence of resistant bacterial infection.

The present invention provides a number of infection-resistant devices, particularly medical devices. These devices in some embodiments include at least one surface comprising a low concentration of gentian violet. In still other embodiments, the device includes a combination of gentian violet and silver nitrate. By way of example, certain embodiments of the invention include at least one silicone surface that includes an antimicrobially and antifungally effective amount of gentian violet. These antimicrobially and antifungally effective amounts of gentian violet are further defined as about 0.008% to less than about 1.0%.

Among the other embodiments, the amount of gentian violet included with the device is about 0.01% to about 0.9%. Even more particularly, the antimicrobially effectively amount of gentian violet constitutes about 0.02% to about 0.09% gentian violet.

Other embodiments of the device include an antimicrobially effective amount of a both silver nitrate and gentian violet. In these devices, the amount of silver nitrate constitutes about 0.08% to about 2.7%, and in still other defined embodiments, from about 0.5% to about 1.0% silver nitrate. The amount of gentian violet will be as defined above, or lower, as it is expected that the gentian violet and silver nitrate will act to enhance the antimicrobial/antifungal activity that is achieved over that observed with each agent alone.

As used in the description of the devices embraced by the present disclosure, calculation of "%" of gentian violet, silver nitrate, or similar substance is based on the amount of agent (e.g., gentian violet in grams) per gram of silicone, polyurethane, or other material of the device.

Any number of devices may include the treatments of the present invention. Such devices, by way of example and not exclusion, include intravascular, peritoneal, pleural and urological catheters, heart valves, cardiac pace makers, vascular shanks, and orthopedic, intraocular or penal prosthesis. Among these, particular applications contemplated for the invention are intravascular and urinary catheters. In the former category, several types of catheters may be considered, such as central venous catheters, peripheral intervenous catheters, arterial catheters, Swan-Ganz catheters, hemodialysis catheters, umbilical catheters, percutaneous nontunnelled silicone catheters, cuffed tunneled central venous catheters, and subcutaneous central venous port catheters.

It should be noted that the preparations of the present invention will also be advantageously used to treat the many different types of medical devices that absorb and/or otherwise retain the herein described gentian violet low concentrations, either alone or together with silver nitrate. By way of example, substances amenable to retention of the disclosed preparations as defined in the present invention include polyethylene, polyurethane, dacron, nylon, polyesters, polytetraflorethylene, LATEX™, silicone, silicone elastomers and the like. Particular envisioned embodiments of the treated medical devices of the invention include at least one surface that is of a silicone or polyurethane material, or a combination thereof.

The present invention also provides particularly advantageous methods for treating a medical device so as to enhance its antimicrobial and/or antifungal resistance. Various methods may be employed to provide this treatment to a medical device. For example, brushing or immersing at least part of the device with the particularly desired preparation of gentian violet, or a combination of gentian violet and silver nitrate, may be employed. Dipping, soaking, or otherwise completely or partially immersing the device or part of the device may also be used in the practice of the present invention.

Gentian violet and silver nitrate, or like agents, may also be mixed at the desired concentrations with a polymeric material prior to preparation of the device or prior to coating the device, to obtain the concentrations specified herein. Devices would then be prepared from this material through an extrusion molding process, or like procedure.

General alternative processes and reagents for bonding an agent contained in a solution to a device are provided in U.S. Pat. Nos. 4,442,133, 4,678,660, and 4,749,595, the entire contents of which are incorporated herein by reference for this purpose. A further method used to coat the surface of medical devices with the subject gentian violet and gentian violet with silver nitrate combination involves first coating the selected surface or surfaces with benzalkonium chloride followed by ionic bonding of the gentian violet or gentian violet with silver nitrate (see, e.g., Solomon, D. D. and Scherertz, R. J. (1987) and U.S. Pat. No. 4,442,133).

Other methods of coating surfaces of medical devices with antibiotics are taught is U.S. Pat. No. 4,895,566 (a medical device substrate carrying a negatively charged group having a pKa of less than 6 and a cationic antibiotic bound to the negatively charged group); U.S. Pat. No. 4,917,686 ("Antibiotics are dissolved in a swelling agent which is absorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders).

These and many other methods can be used for applying gentian violet and gentian violet with silver nitrate preparations to a medical device surface. As is evident, one of ordinary skill having benefit of this disclosure would be apprised of these several different methods of coating any number of medical devices with the subject inventive treatments.

Medical devices, particularly catheters of the type listed in the foregoing table, may be treated with the gentian violet or gentian violet with silver nitrate preparations, and then stored in a sterile packing material until use.

TABLE 1

| Short-term Temporary Access Catheter | Long-term Indefinite Vascular Access Catheters |
|---|---|
| Peripheral Intravenous Cannulas | Peripherally Inserted Contravenes |
| winged steel needles peripheral intravenous catheters | Catheters (PICC) |
| Arterial Catheters | Percutaneous Nontunnelled Silicone Catheters |
| Central Venous Catheters | Cuffed Tunneled Central Venous Catheters (Hickman and Broviac) |
| Swan-Ganz Catheters | Subcutaneous Central Venous Ports (Infusaport, Port-A-Cath, Landmark) |
| Hemodialysis Catheters | |
| Umbilical Catheters | |

While any variety of different methods may be used in providing the medical devices of the present invention, in some aspects the method comprises treating the medical device comprising at least in substantial part silicone or a silicone-like material with a composition comprising between about 0.001% and less than about 1.0% gentian violet in an aqueous solution. A variety of aqueous solutions may be employed. By way of example, such aqueous solutions include distilled water, NaCl, $Na_2H_2PO_4$, KCl, $MgSO_4$, Ca gluconate, dextrose, ranitilide, HCl, and the like. In other embodiments, the method may be described as treating the device with a composition comprising about 0.01% to about less than 1.0% gentian violet in an aqueous solution, rinsing the device (e.g., with water), and drying the device, wherein the device has a gentian violet concentration of about 80 micrograms to about 100 micrograms/gram of silicone. In particular embodiments, the device is to be exposed to a composition of gentian violet for at least about 72 hours at room temperature (about 22° C.).

Alternatively, gentian violet, or a combination of gentian violet and silver nitrate, may be combined with the silicone-like or polymeric material and used to prepare the device, such as by extrusion molding.
Polyurethane Where the device is of a polymeric material, such as polyurethane, particular embodiments of the invention will include an absorbed amount of gentian violet, or similar substance, of between about 0.01% to about 0.10%, or between about 0.02% to about 0.08% or particularly from 0.02% to about 0.05%. The percentage of gentian violet described for the polyurethane materials of about 0.02% to 0.08% constitutes about 200 μg to about 800 μg/gram polyurethane.

In other embodiments, the device may further include a treatment of silver nitrate with a composition comprising about 20% silver nitrate suspended in a non-aqueous solution. By way of example, said non-aqueous solution may comprise alcohol, such as about 70% alcohol.

The invention also provides a combination method for preparing a medical device treated with both gentian violet and silver nitrate. In this method, the medical device comprises silicone or polyurethane, or a mixture thereof, and is treated with a composition comprising about 0.01% to about less than 1.0% gentian violet suspended in an aqueous solution (for example, water), either before or after treatment of the device with a composition comprising about 20% to about 50% silver nitrate suspended in a non-aqueous solution (such as alcohol, particularly about 70% alcohol). Alternatively, both gentian violet and silver nitrate may be prepared in a single composition, and the device exposed to this combination composition for a period of time sufficient to allow the material to attach to the device. By way of example, a solution of about 0.01% gentian violet and about 20% silver nitrate suspended or dissolved in a non-aqueous solution may be prepared and the device or part of the device to be immersed in the solution. The device would include in some embodiments at least one silicone or polyurethane surface. Again, by way of example and not exclusion, the non-aqueous solution in which the gentian violet and silver nitrate is suspended or dissolved may comprise alcohol, such as 70% alcohol, or similar non-aqueous solution suited for said use.

The aforedescribed treatment and methods have been found by the present inventor to provide significantly extended antimicrobial and bacteriostatic action against a variety of common pathogens typically responsible for catheter complications.

Effective bacteriostatic protection is provided employing amounts of gentian violet 5 to 100-fold lower than those previously described. These observations were most unexpected in view of the prior art, which reported much less effective bacteriostatic activity even at much higher concentrations of 1% to 15% G.V. (100-fold higher GV amount than 0.01%). The antibacterial activity is observed to be particularly long-lasting, making said treatments of significant importance in the preparation of long-term catheter implants, as well as in the management of the chronically catheterized or immunologically compromised patient. In addition, the claimed devices with their much lower amounts of gentian violet eliminate the potential for any substantial leaching gentian violet into the blood stream, rendering these devices much more patient compatible.

The aforedescribed preparations and methods have been found effective in preventing the growth of a number of different catheter related pathogens, including by way of example and not exclusion, Staphylococcus (such as *Staphylococcus aureus, Staphylococcus epidermidis*), and fungi (e.g., *Candida albicans*), as well as effective in both treating and eliminating established progressive bacterial infection.

The following abbreviations are used in the description of the present invention:

| G.V. | = | gentian violet |
|---|---|---|
| LRS | = | lactated Ringers Solutions (Ringers - Lactate Solution (RLS)) |
| TPN | = | total parenteral solution |
| $AgNO_3$ | = | Silver Nitrate |
| NM | = | not measurable |
| SN | = | silver nitrate |

Following the long-standing patent law convention, the terms "a" and "an" mean "one or more" when used in the description of the present invention, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A demonstrates the anti-*Staphylococcus epidermidis* activity imparted to silastic after treatment with low GV concentrations. FIG. 2B demonstrates the anti-*Staphylococcus aureus* activity imparted to silastic after treatment with GV. FIG. 2C demonstrates the anti-*Candida albicans* activity imparted to a silastic catheter tubing treated with low concentrations of GV.

FIG. 3A demonstrates the anti-*Staphylococcus epidermidis* activity imparted to a polyurethane surface with and without GV treatment, while FIG. 3B demonstrates anti-*Staphylococcus aureus* activity of surfaces treated with GV or without treatment. FIG. 3C demonstrates the anti-*Candida albicans* activity imparted to a polyurethane surface upon treatment with GV.

DETAILED DESCRIPTION OF THE PREFERRED EMBODIMENTS

Figure 1:
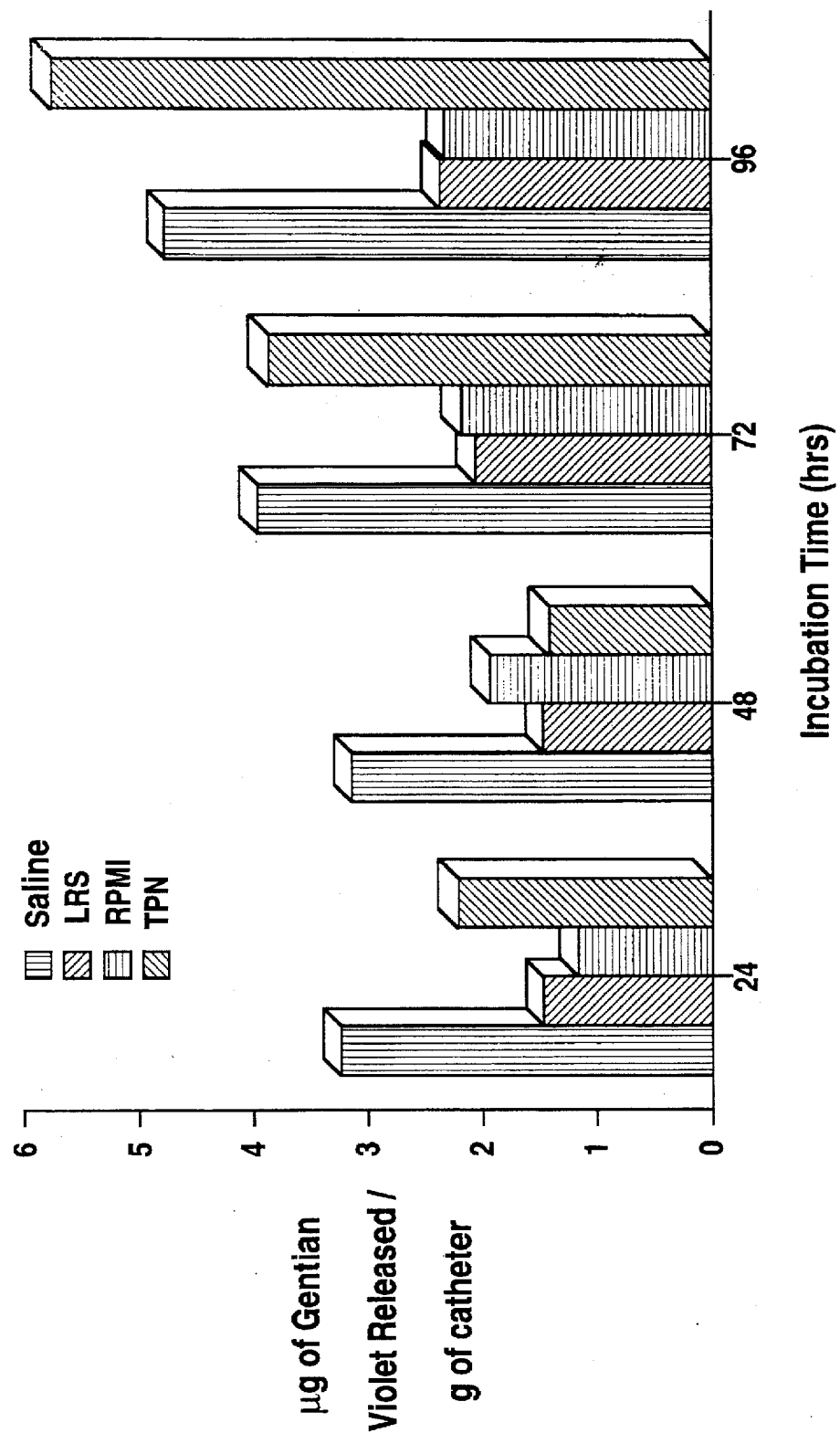
FIG. 1—Graph of the release of gentian violet from GV-treated silicone incubated in different media at 24, 48, 72 and 96 hours. The different media examined were: saline, LRS, RPMI, and TPN. The data demonstrates that in all media examined, there was not an initial "burst" release of gentian violet from the treated silicone. Instead, there appeared a protracted GV release profile over the test period.

The present invention provides effective antibacterial and anti-fungal surface treatments that comprise very low amounts of gentian violet either alone or in combination with silver nitrate. Methods for preparing these devices, which include absorption of GV or GV and $AgNO_3$, to the device are also described.

Virtually any device comprising a material that is capable of absorbing or otherwise retaining gentian violet or silver nitrate may be processed according to the present methods to impart the advantageous properties described here to the device. The long-lasting, antibacterial and anti-fungal activity demonstrated with these treated surfaces render them surprisingly effective against infection, while avoiding the undesirable tissue staining that routinely accompanies use of higher concentrations and/or amounts of gentian violet. This observation was most surprising in view of the prior art, which reported highly variable anti-microbial activity on silicone at concentrations of gentian violet some 5 to 100-fold higher than those employed in the present invention.

The gentian violet used in the present studies was obtained from Sigma Chemical Co. (P.O. Box 14508, St. Louis, Mo. 63178). The silver nitrate used in the studies was also obtained from Sigma Chemical Co. The silicone rubber (SILASTIC®) devices were obtained from Baxter/Scientific Products (210 Great Southwest Parkway, Grand Prairie, Tex. 75050). The polyurethane devices used were obtained from Abbott International Ltd. (One Abbott Park Road, Abbott Park, Ill. 60064–3500). The zone of inhibition protocols used in the present studies, as well as other antibacterial and anti-fungal activity models described here, are well known to those of skill in the art.[3,17,18,19] These standard techniques as described in the art in the referenced articles are specifically incorporated herein by reference.

Culture medium RPMI 1640 was purchased from Roswell Park Memorial Institute. Lactate Ringer's Injection (U.S.P.) and sodium chloride were purchased from McGaw, Inc. (Irvine, Calif. 92714–5895).

The term polymeric material as used in the description of the present invention includes polymers that are capable of absorbing or otherwise retaining gentian violet and/or silver nitrate when exposed to one or both of these materials, particularly at the low concentrations discussed in the present disclosure. By way of example, polymeric materials having these characteristics include those prepared by homopolymerization or copolymerization of hydrocarbons having one double bond, such as ethylene, propylene, 1-butene, 3-methyl-1-butene,3,3-dimethyl-1 butene,1-pentene,4-methyl-1-pentene,3-methyl-1-pentene,1-hexene, 4-methyl-1-hexene,5-methyl-1-hexene,1-cyclohexane, isobutylene,2-methyl-1-pentene, cyclobutene or norbornene.

The term "diene polymer" is also included within the scope of the polymeric material to be treated according to the present invention and, as used in the present invention, means polymers prepared by homopolymerization or copolymerization of hydrocarbons having two double bonds such as butadiene, isoprene,1,3-pentadiene,1,5-hexadiene or 1,6-heptadiene by a known process. By way of example, cis-1, 4-polymer of isoprene, which generally exists as a natural rubber is suitably used in present invention.

Examples of other copolymerizable components include vinyl acetate, methyl vinyl ether, styrene, vinyl chloride, vinylidene chloride, maleic acid anhydride, acrylic acid, methacrylic acid, acrylonitrile, methyl methacrylate, sulfur dioxide, vinylpyridine, chloroprene, ethylene oxide, formaldehyde and polyurethane.

Examples of the silicone polymer used in the present invention include dimethyl polysiloxane, methylphenyl polysiloxane, cyanoalkylmethyl polysiloxane and fluoroalkylmethyl siloxane. Among them, dimethyl polysiloxane may be particularly preferred in the preparation and construction of indwelling medical devices, in view of its high elasticity, high strength and innoxious property.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Absorption, Antimicrobial Activity, and Shelf-life of Gentian Violet Treated Silicone Surfaces The bactericidal effects of treatment with gentian violet, its permanency, and uniformity are demonstrated in the present example. Silastic tubing for all studies was exposed to 0.01% gentian violet solution at room temperature (about 22° C.) for about three days (72 hours) with occasional agitation, rinsed 10 times in water (for injection) (WFI;Abbott International Limited), dried, and gas sterilized. These procedures were carried out under a laminar flow hood using sterile instruments and glassware. A bioreactor will be used for devices to be employed in clinical studies.

Gentian violet was selected as a treatment because of the present inventor's observation that it was capable of inhibiting growth of both gram-positive cocci and yeasts at relatively low concentrations. These organisms are among the most prevalent in catheter- related infections. In contrast to antibiotics, antiseptic dyes frequently possess both antibacterial and fungicidal activity. This beneficial property would preclude Candida overgrowth, the most common occurrence of suprainfection associated with the use of wide-spectrum antibiotics. The gentian violet concentration of 0.01% for the catheter treatment was found to be effective for absorption into silicone material and consequently, for catheter bactericidal activity.

The average amount of gentian violet absorbed by silastic tubing was estimated as about 91/µg/g (or about 100/µg/g) of silastic. The amounts of gentian violet released by one gram of silastic tubing into various media after the current medical practice maximum clinical duration of use (four days) were as follows:

saline—4.72 µg

Ringer's lactate—2.29 µg

RPMI culture medium—2.28 µg total parenteral solution (TPN) solution—5.69 µg.

These values represent 5.2%, 2.5%, 2.5% and 6.2%, respectively, of the total catheter's initially absorbed gentian violet content. The graph of extraction of gentian violet in different media over time is provided at FIG. 1.

All data, obtained by colorimetric measurements, were expressed per weight (gram) of silicone rubber.

Antibacterial Activity—Zone of Inhibition Studies

The specific bactericidal effects of gentian violet-treated SILASTIC® (silicone rubber) catheters were assessed by incubating short segments thereof in agar plates inoculated with different pathogens. Following 48 hours incubation at 37° C. with the four microorganisms most frequently involved in catheter related sepsis, *Staphylococcus epidermidis*, *Staphylococcus aureus*, *Candida albicans* and *Escherichia coli*, the plates were examined and the diameter of inhibition zone was measured.

Figure 2A:
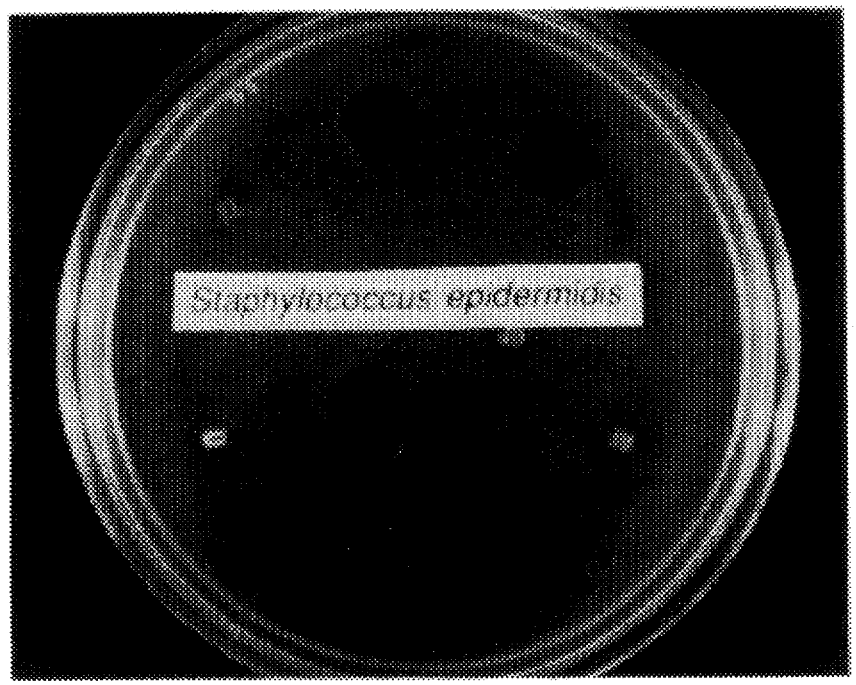
FIGS. 2A, 2B and 2C illustrate the zone of inhibition in examining antibacterial and anti-fungal activity of silastic catheter impregnated with about 0.01% gentian violet in comparison with non-treated controls.
Figure 2B:
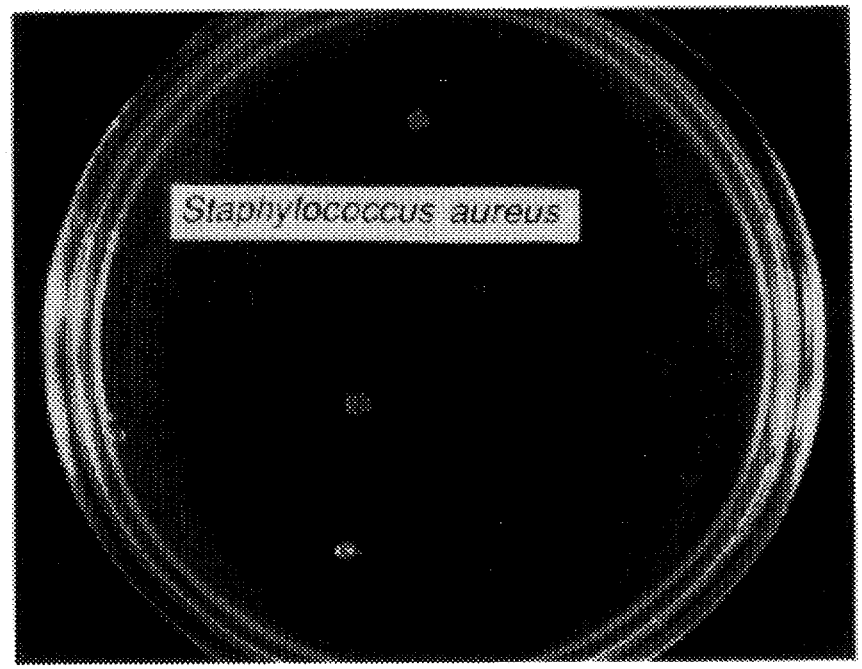
Figure 2C:
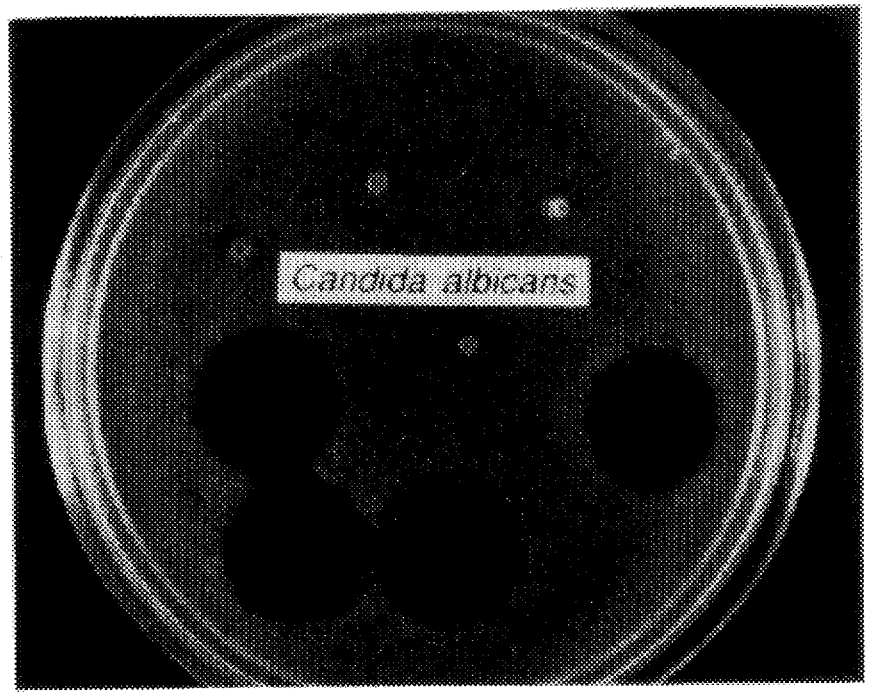

In contrast to the untreated catheters (clear) the gentian violet treated segments (purple) exhibited consistent growth inhibition in three of the tested pathogens (FIG. 2A=*Staphylococcus epidermidis*; FIG. 2B=*Staphylococcus aureus*; FIG. 2C=*C. albicans*; all silastic catheters treated in 0.01% gentian violet).

The effective concentration of gentian violet for optimal absorption to silastic material and an amount of GV that was observed to have significant bactericidal activity was about 0.01% (about 91 µg/g silastic to about 100 µg/g silastic).

Figure 3A:
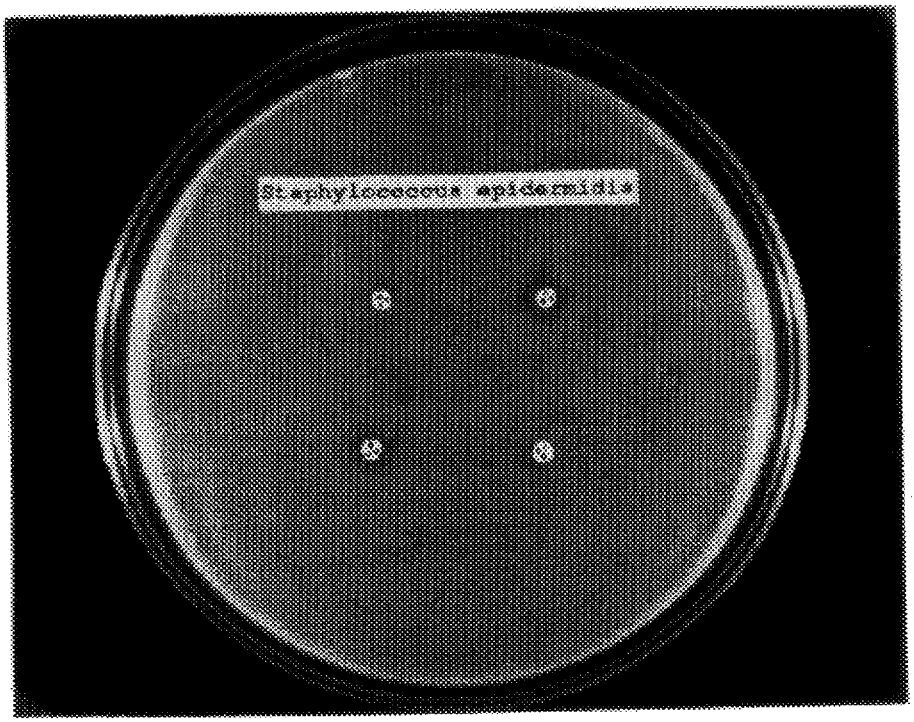
FIG. 3A, FIG. 3B and FIG. 3C demonstrate the antimicrobial activity provided by polyurethane material upon treatment with gentian violet (0.01% GV) in contrast to the same material without treatment.
Figure 3B:
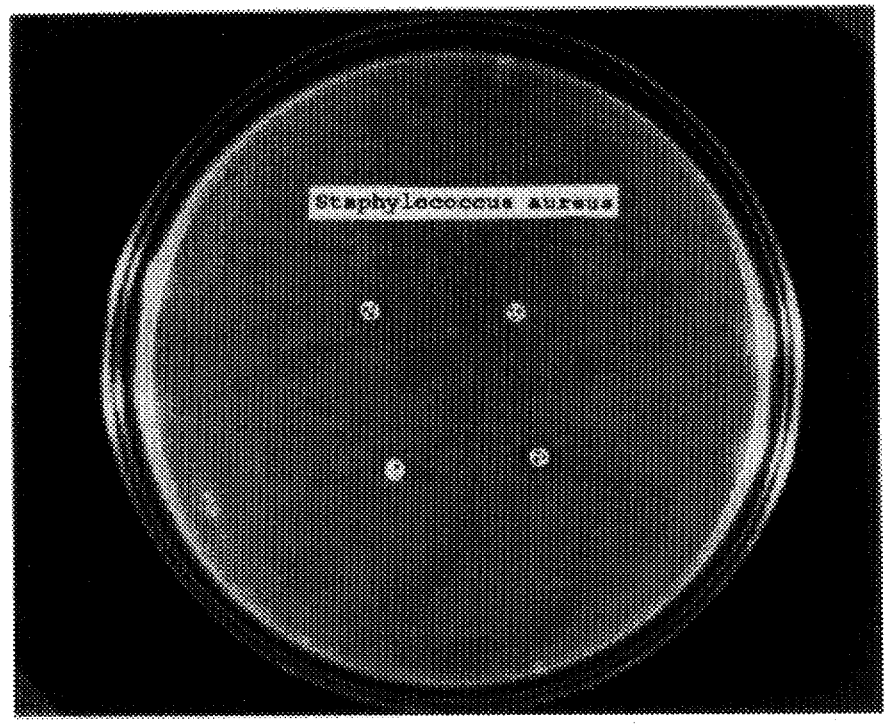
Figure 3C:
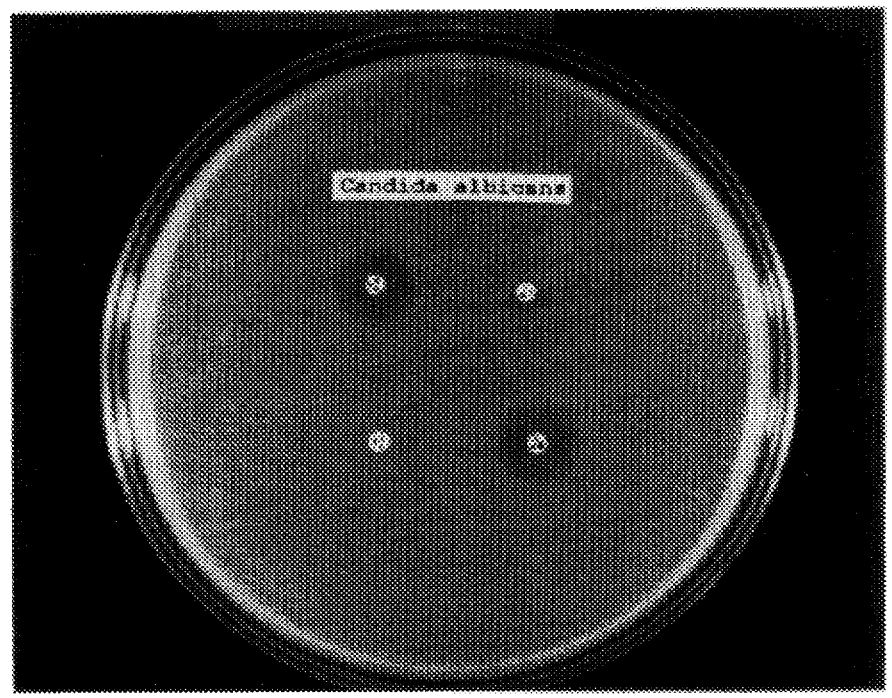

The antimicrobial effect of GV treated catheters was greatest against *Candida albicans* (Inhibition Zone=up to 20 mm); followed by *Staphylococcus epidermidis* (up to 12 mm); and *Staphylococcus aureus* (up to 8 mm) (see FIG. 3).

Shelf Life

The shelf life of the GV treated silastic product was tested using G.V. treated catheter segments. The treated (G.V.) and control (no G.V.) segments were gas sterilized and stored at room temperature for 30 or 60 days; following this storage period, the segments were removed and placed in agar plates inoculated with one of the four microorganisms used to test the catheter potency in the reports above.

Following a 30 day storage period, a strong bactericidal activity against the gentian violet-sensitive organisms (*Candida albicans*, *Staphylococcus aureus*, *Staphylococcus epidermidis*) was observed in all the specimens. This activity was observed to diminish after 60 days. However, inhibition of *Candida albicans* and *Staphylococcus aureus* organisms was still evident. Since the culture of *Staphylococcus epidermidis* was contaminated with *E. coli*, the anti-*Staphylococcus epidermidis* activity in these cultures could not be determined at the 60 day test point.

Absorption of Gentian-Violet to Silicone Rubber

The uniformity of gentian violet absorbance to a catheter was shown in the following studies. Ten silicone catheter segments with an approximate length of 1 cm were randomly cut from five gentian violet-treated catheters treated as described above. The segments were weighted, ($x=0.03247$ g), placed into tubes containing 1 ml of glacial acetic acid (99.8%), covered and heated to 100° C. for two hours in a boiling water bath. The resulting extracts were serially diluted and the amounts of gentian violet released into the acid were determined spectrophotometrically at wavelength of 590 nm (Beckman spectrophotometer, model DU60). When normalized for segments weight, the released amounts averaged 83.73 µg/g which represented 92% of the dye initially absorbed by the treated catheters. The normal distribution, i.e., the uniformity of gentian violet amounts absorbed per gram of silastic material, was tested for a hypothesis that the observed differences from the mean were not statistically different from zero. On the basis of the t-test results, the null hypothesis was accepted with the assumption that the dye content in the random catheter samples was approximately equal, or represented a population with a normal distribution, confirming the uniformity of gentian violet absorption.

EXAMPLE 2

Stability of Gentian Violet Treated Silicone Catheters

The effect of sterilization on catheter bactericidal potency against three gentian violet-sensitive pathogens is demonstrated in the present example.

Anti-Bacterial Stability

Steam sterilization resulted in decreased antibactericidal activity against all three pathogens examined. However, gas sterilization did not produce any changes in bacteriostatic activity from the pre-sterilization levels.

Tensile Strength and Stability

A total of eight specimens (four GV "treated" and four "untreated") were tested for strength after treatment and sterilization. Each specimen was cut into 2" long pieces and placed in a specially designed gripping fixture. The grips provided enough force at the end of the specimen to prevent slipping without crushing the material. The grip/specimen assembly was then placed in a loading frame and pulled until the tubing broke. The maximum load and elongation at failure point were recorded for each specimen.

Results

The following table presents the test results in the form of maximum load and total elongation at failure point.

TABLE 2

|  | Max. Load (lbs) | Max. elongation (%) |
|---|---|---|
| Treated tubing | | |
| Run-1 | 2.00 | 6.85" (343%) |
| Run-2 | 3.00 | 7.45" (373%) |
| Run-3 | 2.75 | 7.10" (355%) |
| Run-4 | 2.80 | 6.35" (318%) |
| Untreated tubing | | |
| Run-1 | 2.00 | 5.60" (280%) |
| Run-2 | 2.00 | 4.80" (240%) |
| Run-3 | 2.80 | 7.85" (393%) |
| Run-4 | 2.25 | 5.55" (278%) |

In summary, the treatment did not diminish the tensile strength of the catheters; in fact, treated segments withstood a slightly higher maximal load than their untreated counterparts ($\bar{x}$=2.638 lb. vs 2.263 lb.; p<0.242). The treated catheters also demonstrated elasticity similar to the controls as documented by the maximal elongation values for critical load (6.94" vs. 5.95"; p <0.207).

EXAMPLE 3

Anti-Fungal Activity of G.V. Treated Silastic

The present example demonstrates the significant anti-fungal activity of low concentrations of gentian violet on or absorbed into a silicone material.

Both GV treated and control catheters were incubated in *Candida albicans*-inoculated plasma at 37° for nine days. *Candida albicans* was suspended in 10 ml of plasma to achieve an initial concentration of approximately $1 \times 10^6$ colony forming units (CFU) per milliliter. Five milliliters of the inoculated plasma were added to two sterile tubes containing catheter segments (control or treated); the tubes were lightly capped and agitated. Both tubes were drained at 24 hour intervals and refilled with 5 milliliters of newly inoculated plasma. Three catheter segments and small aliquots (10 microliters) of inoculated plasma were taken from each tube at three day intervals. The segments were carefully dried by gentle blotting on sterile filter paper, transferred separately into sterile tubes containing 2 milliliters of sterile PBS and sonicated (Sonicater® by Heat Systems-Ultrasonic Inc.) on ice for one minute to release the associated microorganisms. The saline wash and the plasma samples were then serially diluted and cultured for 24 hours to obtain colony counts. The results of these experiments (expressed as log CFU) are summarized in Table 3.

The differences between the CFU in plasma samples (5,215,057 for controls and 2,505,481 for treated catheters) and between the means of results from triplicate catheter segments (106,535 for controls and 74,196 for treated) were analyzed for statistical significance using Wilcoxon signed rank test. Plates with too numerous colonies to count (TNTC) could not be used in statistical analysis; since they have occurred in control samples only, they actually have provided a bias against the treated catheters. The differences between the numbers of *Candida albicans* both in the plasma and associated with silastic segments, were highly significant (p<0.003 and p<0.006, respectively).

TABLE 3

IN VITRO EXPERIMENTS Effect of catheter treatment on *Candida albicans* in in vitro experiments

| | PLASMA (LOG CFU) | | CATHETERS (LOG CFU) | |
|---|---|---|---|---|
| | CONTROL | TREATED | CONTROL | TREATED |
| | TNTC* | 3.40* | 3.03 | 2.58 |
| | TNTC* | 3.48* | 2.92* | 0 |
| | 3.97 | 3.98 | 2.89 | 3.26 |
| | 2.92 | 2.99 | 3.49 | 3.26 |
| | 3.09 | 2.73 | 3.27 | 2.11 |
| | 5.54 | 4.54 | 5.85 | 4.94 |
| | 7.62 | 7.28 | 3.35 | 3.98 |
| | 7.10 | 6.60 | 3.02 | 2.04 |
| | 3.08 | 2.69 | TNTC* | 3.59* |
| | TNTC* | 3.03* | 3.88 | 1.81 |
| | 5.17 | 4.45 | 3.40 | 2.76 |
| | 2.80 | 5.56 | 3.39 | 2.67 |
| | 6.02 | 5.76 | 3.24 | 2.58 |
| | 5.64 | 4.93 | 5.79 | 5.25 |
| | 7.10 | 6.86 | 3.90 | 4.61 |
| | 7.10 | 7.17 | 4.85 | 3.94 |
| | TNTC* | 3.48* | 3.06 | 1.72 |
| | 3.48 | 3.40 | 2.31* | 0* |
| | 4.19 | 3.85 | 3.81 | 3.34 |
| | 5.99 | 5.88 | 3.19 | 3.03 |
| | 5.86 | 5.19 | 3.43 | 2.47 |
| | 5.74 | 5.94 | 6.00 | 6.10 |
| | 7.16 | 6.11 | 3.93 | 4.52 |
| | 6.81 | 5.88 | 4.03 | 4.87 |
| Mean | 5.32 ± 0.36 | 5.09 ± 0.33 | 3.85 ± 0.21 | 3.39 ±0.27 |
| N | 20 | 20 | 21 | 21 |
| Wilcoxon Spread Rank Test | 32.00 | | 44.00 | |
| Significance | p < 0.003 | | p < 0.006 | |

EXAMPLE 4

In Vivo Antimicrobial Activity of GV-Treated Silastic Catheters

In these studies, the effects of GV-treated catheters on the in vivo catheter colonization of *Candida albicans* were assessed. The choice of this particular pathogenic organism for these studies was related to the fact that Candida infections are encountered in the most seriously ill burn patients and, therefore, represent an extremely high risk of catheter related complication, and because they are the most difficult to treat.

The development of a suitable in vivo experimental model with extended exposure of catheters to Candida microorganisms was developed. In healthy laboratory animals, Candida introduced into the blood stream was rapidly cleared; when larger doses were administered an overwhelming infection with precipitous death ensued. Consequently, the previously used model[3] with intravascular implantation of the catheters and subsequent administration of pathogen in doses sufficient to produce extended bacteremia could not be established. In the present model, the catheters were placed inside a semi-permeable polytetrafluoroethylene (PTFE) capsule, normally used for vascular grafts, in an effort to simulate a miniature incubator (or abscess) with access only by body acellular fluids. Following infiltration by connective tissue, PTFE material was expected to exhibit basic sieving properties of the vascular wall, excluding proteins and blood particles. The capsules retained microorganisms while allowing nutrients and substances with low molecular weight to cross the wall. This was based on preliminary in vitro experiments with *Escheri-* chia coli. The Candida organisms, installed into the implanted capsule, survived for nine days without supplemental nutrients and remained localized in the catheter surrounding fluid without any symptoms of systemic bacteremia or sepsis. In this fashion, a long-term, limited but controlled environment inducive to catheter colonization was maintained for the in vivo experiment's duration.

The details of the in vivo studies may be summarized as follows: Gortex tubing for the capsule (Cortex expanded PTFE—9 mm OD) was cut into 15 mm pieces with one end sealed by heat. Four silastic catheter segments (5 mm length), either pretreated by 0.01% solution of gentian violet or control, were inserted into the capsule which was then gas-sterilized. Following injection of Candida albicans (approximately $2 \times 10^4$ organisms per capsule) in PBS (0.15 ml), the capsules were completely sealed with heat and implanted into animals in the manner described below.

Under pentobarbital anesthesia (intraperitoneal administration: 50 mg/kg for male rats, 40 mg/kg for female rats), capsule containing both the control and the treated segments were placed into the peritoneal cavity of rats. On days 3, 6 and 9 following the implant, one treated and one control capsule were removed. The number of organisms in the capsule fluid and on the surface of the catheters (following vortex and sonication treatments in 2 ml of sterile PBS) was determined using serial dilutions in a drop plate method on appropriate agar plate (Sabourand Dextrose Agar [DIFCO]). The results, expressed as a mean of triplicate CFU counts corrected for appropriate dilution, are presented in Tables 4 (capsule fluid=initially RPMI 1640 culture medium) and 5. The data, further analyzed for statistical significance of the differences by Wilcoxon signed rank test, confirmed those from in vitro investigations: catheters pretreated with gentian violet demonstrated a long-term bactericidal activity against *Candida albicans*.

TABLE 4

Effect of catheter treatment on *Candida albicans* in capsule fluid in in vivo experiments

|  | Day 3 | | Day 6 | | Day 9 | |
|---|---|---|---|---|---|---|
|  | CONTROL | TREATED | CONTROL | TREATED | CONTROL | TREATED |
|  | 44,000* | 34,000 | 8,000 | 7,000 | 120,000 | 40,000 |
|  | 29,000 | 10,000 | 24,000 | 18,000 | 18,000 | 12,000 |
|  | 56,000 | 36,000 | 40,000 | 40,000 | 9,000 | 1,000 |
|  | 66,000 | 31,000 | 4,000 | 12,000 | 15,000 | 8,000 |
|  | 210,000 | 60,000 | 63,000 | 56,000 | 37,000 | 40,000 |
|  | 270,000 | 170,000 | 14,000 | 46,000 | 81,000 | 45,000 |
|  |  |  | 42,000 | 56,000 | 84,000 | 56,000 |
|  |  |  | 170,000 | 140,000 |  |  |
|  |  |  | 130,000 | 110,000 |  |  |
| MEAN | 112,500 | 56,833 | 55,000 | 53,889 | 52,000 | 28,857 |
| STANDARD ERROR | 41,365 | 23,546 | 18,009 | 14,101 | 16,248 | 8.078 |
| n | 6 | 6 | 9 | 9 | 7 | 7 |
| WILCOXON SIGNED RANK TEST | 0.000 |  | 17,500 |  | 1.000 |  |
| SIGNIFICANCE | p <0.014 |  | p <0.472 |  | p <0.014 |  |
| % Ctrl > Trt | 100.000 |  | 55.6 |  | 85.7 |  |

*All data are reported as colony forming units of a triplicate determination.

TABLE 5

Effect of catheter treatment on *Candida albicans* associated with catheter segments in vivo experiments

|  | Day 3 | | Day 6 | | Day 9 | |
|---|---|---|---|---|---|---|
|  | CONTROL | TREATED | CONTROL | TREATED | CONTROL | TREATED |
|  | 10,950* | 4,500 | 1,840 | 890 | 910 | 372 |
|  | 1,375 | 687 | 915 | 190 | 1,425 | 595 |
|  | 7,650 | 5,575 | 8,750 | 6,182 | 1,225 | 192 |
|  | 12,520 | 56,40 | 565 | 742 | 1,990 | 930 |
|  | 3,997 | 4,145 | 7,162 | 3,780 | 1,622 | 1,702 |
|  | 10,050 | 6,042 | 1,812 | 902 | 2,902 | 1,910 |
|  |  |  | 4,920 | 3,962 | 3,730 | 3,262 |
|  |  |  | 760 | 1,172 |  |  |
|  |  |  | 2,550 | 3,212 |  |  |
| MEAN | 7,757 | 4,432 | 3,253 | 2,337 | 1,972 | 1,280 |
| STANDARD ERROR | 1,761 | 806 | 1,063 | 714 | 380 | 411 |
| n | 6 | 6 | 9 | 9 | 7 | 7 |
| WILCOXON SIGNED RANK TEST | 1.000 |  | 6.000 |  | 1,000 |  |

TABLE 5-continued

| | Effect of catheter treatment on *Candida albicans* associated with catheter segments in vivo experiments | | | | | |
|---|---|---|---|---|---|---|
| | Day 3 | | Day 6 | | Day 9 | |
| | CONTROL | TREATED | CONTROL | TREATED | CONTROL | TREATED |
| SIGNIFICANCE | p <0.023 | | p <0.025 | | p <0.014 | |
| % Ctrl > Trt | 83.3 | | 77.8 | | 85.7 | |

*All data are reported as colony forming units of a triplicate determination.

Toxic Side Effects

The possibility of toxic side-effects of treated catheters on the surrounding vessels was also assessed. Treated and control catheters (10 mm in length—1.19 mm OD) were placed in the jugular veins of rats under pentobarbital anesthesia. Ten days following the implant, the animals were sacrificed and the catheters and associated veins excised. Fourteen implants were examined for histological changes due to the presence of treated catheters on the surrounding vessels. The microscope evaluation of the vein segments (0.5 to 0.7 cm in length and 0.1 to 0.3 cm in diameter) was summarized. Serial transverse sections demonstrated either minimal or mild lymphocytic infiltration in the venous wall and organizing or organized thrombi were frequently seen in the lumens. There was no significant difference in the degree of inflammatory reaction in the venous walls of the control and test specimens.

DETAILED DESCRIPTION OF PROTOCOL FOR IN-VIVO STUDY

MATERIALS AND METHODS
CAPSULES

1. Gore-Tex expanded PTFE tubing (3.2 cm circumference) was cut into 1.2 cm segments [1.5cm segments for thicker tubing]. Silastic tubing (control and treated) was cut into 0.5 cm segments [Dow Coming, 0.040 in. ID and 0.085 in. OD, Cat#602–205]. One side of the Gore-Tex segment was heated and sealed completely with a hemostat and Bunsen burner. Four silastic tubing segments were placed into each Gore-Tex capsule using forceps (all control or all treated in each). The other end of the Gore-Tex capsule was then sealed, but a small opening was left open in the corner. The finished product was placed in a plastic tube for gas sterilization.

2. *Candida albicans* was cultured in Sabourand (SAB) liquid media overnight, spun down the next day, and the media poured off. Candida was then washed once with sterile saline. Approximately 2 to 3 ml RPMI was added to resuspend cells. A hemocytometer was then used to count Candida, and the cells were diluted to $2 \times 10^7$/ml. With a 1 ml syringe, 0.1 ml of the Candida solution was delivered to each capsule, taking care there were no air bubbles. The opening of each capsule was then sealed with a heated hemostat. As prepared, the capsule was ready for intraperitoneal (ip) implantation.

CATHETERS:

1. Silastic tubing [Dow Corning, 0.012 in. ID×0.025 in. OD, cat#602–105] (control and treated) was cut into 1 cm segments. About 2 cm of Ethibond 3-0 green braided polyester suture was threaded through each one, and sterilized as described above for capsule. The tubing was then ready for implantation in a rat for nine days.

SURGERY

1. Each rat was weighed and anesthetized with pentobarbital (ip).

2. The skin of the abdomen and neck were washed with betadine solution. Using sterile instruments, the neck area was opened first. The right and left internal jugular veins were then exposed. While cannulating the first jugular vein, a 2.0 ml sample of sterile blood was collected, being very careful not to puncture the vein. The blood was put into a 12×75/mm sterile snap cap tube. One hundred µl of the blood was pipetted (with sterile pipette) into another sterile tube. This was used for Candida culture. The large sample was then centrifuged for five minutes. Plasma was then pipetted off (with sterile pipette) into 2 sterile tubes of the same size as above.

3. Each internal jugular vein was cannulated and the catheters inserted. When the catheter was inserted fully into the vein, the top was tied off with suture already in place. When both catheters were securely in place, the neck area was closed.

4. A small incision (approximately 1 inch long) was made in the skin down the center of the abdomen. A cut (about ½ inch long) down the center of the muscle layer into the abdomen was then made. Four capsules were inserted into each animal (2 on each side). The muscle layer and the skin layer were then closed.

5. Candida Blood Culture: Using a sterile Pasteur pipette, about 50 µl (½) of the blood sample was placed onto each of two SDA (Sabourand dextrose agar) plates. Each tube was flushed with a small amount of sterile saline and added to each plate. Using a bacteriological loop, each blood sample was spread over the agar plate evenly. Each plate was checked for bacterial growth on days 3, 6 and 9 after inoculation.

DAYS 3, 6, AND 9

1. Preparation

4 Petri Dishes: 2 ml of sterile saline was pipetted into 2 petri dishes. The plates were labeled "C" for Control and "T" for Treated. A third petri dish with some sterile saline was prepared for placing the capsules after removal from the abdomen and removing the host tissue. Another petri dish with sterile saline was prepared to rinse off the forceps between capsules.

2. Surgery

Day 3 or Day 6—Rats were anesthetized with pentobarbital ip. Sutures from the previous surgery were opened. The capsules (1 control, 1 treated) were then removed from the abdomen and placed into a sterile petri dish. Another 2 ml of sterile blood needed at this time was collected from the hepatic vein. 100 µl of the blood was placed into a sterile tube and centrifuged. A Candida blood culture was performed.

Day 9—Anesthetize rat with pentobarbital IP. The abdomen was opened and the last two capsules retrieved and placed in a sterile petri dish. Another 2 or 3 ml of sterile blood sample from the vena cava was collected. Catheters and surrounding vein tissue were also removed from the neck area. These capsules and tissues were then stored in formaline. A Candida blood culture and cultures from the segments were prepared as before.

3. Culture Preparation

Host tissue was removed from the capsule with sterile forceps. Each capsule was placed into prepared and marked petri dishes. With sterile instruments, an open seal was cut on one side and the four segments placed in saline. All fluid was removed from these segments, inside and out with sterile filter paper. Each segment was stored in vortexed tubes containing 2 ml of sterile saline. Each tube was vortexed for 30 seconds making sure the segment was immersed in the fluid. Segments were removed and drained as before, placed into a sterile glass vial with 2 ml of sterile saline, and sonicated for 30 seconds at 25 Hz. Each capsule was flushed with saline from the petri dish. All fluid was transferred into corresponding fluid tubes.

Following serial dilutions, droplets of both the capsule fluids and from the segment wash fluid were plated on SDA-containing petri dishes, and incubated for 48 hours. CFU on each plate were counted and corrected for the dilution used.

PROPHETIC EXAMPLE 5

Human Trials

In the presently described study, GV, an antimicrobial agent that is not an antibiotic, will be used for pretreatment of catheters to be utilized for hemodynamic monitoring and total parenteral alimentation of patients in UMC Burn and SICU Unit. The bactericidal and fungicidal effectiveness of these catheters has already been tested in both in vitro and in vivo experimental studies. Based on an unchanged admission rate in ICUs, it can be expected that during this period of time, over 400 subjects (200 for implantation of the treated and 200 for the control catheters) will be examined.

All patients admitted to the Burns and Surgical Intensive Care Units will be clinically evaluated as to the need for invasive hemodynamic monitoring and/or parenteral nutrition. Accepted indications for central venous cannulation will include central venous pressure measurement, pulmonary artery and wedge pressure monitoring/cardiac output determination, vasopressor administration, parenteral nutrition and urgent intravenous access. In addition to severe burns, the clinical situations mandating invasive hemodynamic monitoring will also include cardiogenic shock, hemorrhagic shock, septic shock, adult respiratory distress syndrome, respiratory insufficiency with mechanical ventilation dependence and multisystem organ failure. The standard indications for invasive hemodynamic monitoring or treatments in any of the patients will not be altered due to their inclusion in the study protocol.

Patients admitted to the Surgical and Burn Intensive Care Units requiring long-term intravascular access for monitoring or therapy will be divided into two groups. The subjects will be randomized and assigned to two groups. In the first group, commercially available and routinely used catheters will be used. The same type of catheters will be used for catheterization in the GV study group: these catheters will be impregnated with 0.01% gentian violet solution. Following this treatment, the catheters will be thoroughly rinsed with sterile saline and air dried. They will be then individually sealed in sterilization bags and gas-sterilized in the central sterilization unit prior to use.

Upon discontinuation of hemodynamic monitoring, catheter tips will be cultured. Using sterile instruments, two-inch segments of distal catheter will be separated and transferred into a sterile container to be transported to the clinical laboratory (already standard protocol for central venous catheters).

In the event of overt clinical sepsis in any group without evidence of a specific source, the indwelling intravascular cannula will be removed, the catheter tip cultured and two peripheral blood cultures obtained. If clinically mandated, a new catheter will then be inserted via a new insertion site. Demographic information will be obtained on each patient. Specific parameters that will be followed will include patient's age, sex, extent and severity of the injury, underlying medical illness, indications for invasive hemodynamic monitoring, vascular access site(s), complications during catheter insertion an catheter tip culture results. Concurrent infections, transfusions, fluid administrations and therapy, including antimicrobial efforts will also be recorded. Statistical analysis will be performed to test the hypothesis that the experimental group will have less colonization than the control group.

All statistical tests will be considered significant at $p=0.05$. Statistical analysis will be done using the Statistical Analysis System (SAS) version 6.08, Cary, N.C. Depending on the nature of the distribution of the mean number of colonies, either a t-test for independent samples or a two-sample nonparametric test (Wilcoxon rank-sum test) will be used to determine if there is a difference between the control and experimental groups.

There will be no additional procedures, discomfort or risks incurred as a result of participation in the study. All catheter insertion will be performed when indicated under the standard protocol; both the treated and untreated intravascular catheters will remain in place until the patient no longer requires monitoring. Dressing changes and line care will be performed according to standard acceptable nursing protocol for both groups and the indications for hemodynamic monitoring and/or intravascular administrations will be reassessed to determine the continued clinical need in the patients.

The possible risks associated with the pretreatment of the commercially-produced catheters by 0.01% gentian violet are expected to be negligible. The majority of reported complications pertain to rare cases of oral mucous membrane lesions in neonates following frequent treatments (5–12 times daily) with 0.5% to 2% solution of gentian violet. In most of the cases, only a reduction of solution strength and application frequency was recommended to remedy the problems. The only reported gentian violet intravascular application was its use as blood additive to prevent transmission of Chagas disease. The agent was used in 0.04% concentration and no complications were reported.

The concentration of gentian violet used to treat the catheters in the present study is lesser than that recommended for clinical use (0.01% vs. 0.04%). Furthermore, the catheters are thoroughly washed and rinsed prior to their sterilization and use. To assess the amount of gentian violet which may dissociate from the catheter, 2 cm of treated segments were incubated in 5 ml of saline at 37° C. for seven days and the medium was colorimetrically measured for gentian violet content. The final concentration in this small volume reached 0.00007%, approximately 1/500th of solutions used clinically, without any reported complications.

Description of device

The treated catheters will have the same physical properties as the non-treated catheters, routinely used for monitoring and treatment in ICU's. As reported above, the treatment with low amounts of gentian violet did not change apparent mechanical qualities of the catheters, the only difference was a change of color (light violet shade) of the material.

The facilities used for gentian violet treatment, complying with good laboratory practice requirements, are already established in the Department of Surgery at Texas Tech University Medical School. The major equipment used in the studies will include the following:

a) sterile room (class 100) with air exchange system (7×hours) through 0.1 um HEPA filters, and with controlled environment (10 °–15° C., relative humidity 20%). Floor, walls and ceiling are covered by materials capable of easy sterilization and endotoxin removal. Protocol for sterilization (UV, gas, ethanol, E-Toxa-Clean) and protocol for continuous detection of endotoxin in all room areas will be developed.

b) sterile cold room (minimum class 100) with air exchange system (2×hours) through 0.1 um HEPA filters and with a controlled environment (0°–10° C., Relative Humidity 0–20%). Protocol for sterilization (UV, gas, ethanol, E-Toxa-Clean) and a protocol for continuous detection of endotoxin in all cold room areas will be developed.

c) major equipment:
Laminar flow hoods (class 10) with 6 meter stainless steel working area.
Deep freezer unit (up to —90° C.) and refrigerator.
Waters/Millipore ultrafiltration systems (various).
Sterilizer with 100 liter chamber (pressure 20 p.s.i. and temperature 254° F.).

EXAMPLE 6

Description Of The Methods, Facilities and Controls Used For Manufacturing, Processing, Packing, Storage And Installation Of The Device.

The catheters are treated by soaking in 0.01% gentian violet (prepared form stock supplied by Sigma [C. 1.42555] using water from Millipore Ultrafiltration Systems), for 72 hours. Following the treatment, catheters are rinsed in 10 changes of water (Type I organic free). The catheters are then dried in a laminar flow hood, repacked in their original packaging material, marked, and gas sterilized.

EXAMPLE 7

Solubility Of Gentian Violet In Alcohol-Containing Media

The present example examines the solubility of G.V. in various concentrations of alcohol-water mixtures. The results of these preliminary tests were expected to have an impact on the possibility of simultaneous treatment of a catheter with both the gentian violet and $AgNO_3$ since alcohol has previously provided better medium for absorption of $AgNO_3$ into silastic (even though the agent's solubility in alcohol is less than in water).

In the first test, the concentration of gentian violet was constant (1.00%) while the alcohol concentration in the solvent varied from 0% to 70%. The use of water or lower concentrations of alcohol (0% and 5%) led to slow and incomplete dissolution, signified by presence of clumps. The higher concentrations, including the 70% solution previously used to impregnate silastic catheters with $AgNO_3$, resulted in a complete and fast dissolution of the dye.

TABLE 6a and 6b

Absorption and early elution of Gentian Violet as a function of its concentration and alcohol content in the treatment solution

| | Treatment (days 1 to 7) | | | Resulting color (day 8) | |
|---|---|---|---|---|---|
| | Gentian Violet (%) | Alcohol (%) | Alcohol/Gentian Violet ratio | Catheter | LRS soak* (24 hrs) |
| 6a | 0.01 | 70 | 7000 | light purple | 1+ |
| | 0.10 | 70 | 700 | purple | 3+ |
| | 1.00 | 70 | 70 | dark purple | 5+ |
| | 2.00 | 70 | 35 | dark purple | 5+ |
| 6b | 0.01 | 25 | 2500 | purple | 5+ |
| | 0.01 | 70 | 7000 | light purple | 1+ |
| | 0.01 | 95 | 9500 | gray | 2+ |

EXAMPLE 8

Absorption and Release of G.V. From Polyurethane as a Function of the Alcohol Content in the Treatment Media The absorption of gentian violet to polyurethane (estimated from the resulting catheter color), under conditions of constant solvent composition (70% alcohol) paralleled its concentration in the impregnating media (Table 6a). However, with the increasing concentration of the dye, the amount subsequently released into the aqueous media (LRS) over 24 hours incubation also increased (color of the soaking media was rated by comparison with standards from 0+ to 10+; 0+=less than 1 ng/ml; 10+=equal or higher than 10 ng/ml). Under the conditions of constant gentian violet concentration (0.01%) and varying alcohol (Table 6b), another relationship between the absorption (color) and the composition of the treatment fluid has become apparent. By increasing the alcohol/gentian violet concentration ratio, the physio-chemical properties of the gentian violet and its bond to polyurethane appeared to have changed, resulting in a lesser and modified absorption (gray color) to the catheter and subsequently decreased apparent elution of the dye.

EXAMPLE 9

Long-term Elution of Gentian Violet From Polyurethane Into LRS as a Function of the Alcohol Content in the Treatment Media The long-term wash out from polyurethane catheters, treated again for a week in solutions with varying gentian violet and alcohol contents is illustrated in Table 7. The elution into aqueous solution (LRS) from catheters impregnated with the highest gentian violet concentrations was more pronounced and lasted longer following the treatment in which no alcohol or only low concentrations (5%–25%) were used. When a second treatment with or without alcohol was added before LRS solution, catheters initially treated with solution of high gentian violet concentration in 70% alcohol released approximately twice as much of the dye to the alcohol solutions (70%) than to water. This same phenomenon was noted regardless of addition of other components (as $AgNO_3$) into the treatment liquid (Table 8).

No further elution was noted from catheters exposed during the second treatment to alcohol (samples 2 and 4) into the aqueous media (LRS), while slight release of the gentian violet from catheters exposed to water continued for another 10 days. The amount of gentian violet released over this period of time was similar to those from catheters exposed only to one treatment with gentian violet (sample #5).

These results suggest that addition of alcohol to the treatment solution facilitates not only the absorption but also the subsequent release of gentian violet to media of similar composition. In view of the fact that the release of gentian violet from bioimplants, including catheters, would be in aqueous millieu (plasma and interstitial fluids) the addition of alcohol in some steps of the treatment may have some additional beneficiary effect on improved in situ retention of the dye.

TABLE 7

Release of Gentian Violet Into Aqueous Solution (LRS) from Catheters Treated in Various Concentrations of G.V. and Alcohol
Catheter treatment days 1–7; continuous soaking

| | Catheter Color | | | | | |
|---|---|---|---|---|---|---|
| | Day 7 | Day 8 | Day 9 | Day 10 | Day 11 | Day 12 |
| 0% Alc | | | | | | |
| 0.01% GV | 3± | NM | NM | NM | NM | NM |
| 0.10% GV | 5± | NM | NM | NM | NM | NM |
| 1.00% GV | 5± | 2± | 2± | 1± | 1± | NM |
| 5% Alc | | | | | | |
| 0.01% GV | 3± | NM | NM | NM | NM | NM |
| 0.10% GV | 5± | NM | NM | NM | NM | NM |
| 1.00% GV | 5± | 1± | 2± | 1± | 1± | NM |
| 25% Alc | | | | | | |
| 0.01% GV | 2± | NM | NM | NM | NM | NM |
| 0.10% GV | 4± | NM | NM | NM | NM | NM |
| 1.00% GV | 5± | 2± | 2± | 1± | 1± | NM |
| 70% Alc | | | | | | |
| 0.01% GV | 1± | NM | NM | NM | NM | NM |
| 0.10% GV | 2± | NM | NM | NM | NM | NM |
| 1.00% GV | 4± | 1± | 1± | NM | NM | ± |

NM = non-measurable and *Staphylococcus aureus*, were used to demonstrate the treatment's antimicrobial and antifungal characteristics and to compare and contrast these with those provided by commercially available Arrow catheter.

In this study, polyurethane catheters (10 cm length) were treated in a gentian violet/water solution having a concentration of 0.01 for seven days at room temperature, then rinsed 10 times with water for injection (WFI, Abbott), and allowed to dry. Each catheter was cut into 2 mm segments and gas sterilized. Similar segments were prepared from Arrowgard™ Blue Line central venous catheters (containing silver sulfadiazine and chlorhexidine). Three segments from each catheter were then placed in a plate of agar containing therein one of *C. albicans*, *E. coli* or *Staphylococcus aureus* microorganisms. The remaining segments of each catheter were then soaked in 2 ml. of LRS for nine days. Triplicate segments of each catheter were removed at days 3, 5, 7 and 9 and plated; inhibition zones around the segments were measured with the results demonstrated in Table 9 below.

TABLE 9

Short-term bacteriostasis Effects of Gentian Violet-treated Polyurethane as Compared with Arrow Antiseptic Catheters
Zone Inhibition (diameter in mm)

| | C. albicans | | E. coli | | S. aureus | |
|---|---|---|---|---|---|---|
| Day | Ag | Arrow | A-g | Arrow | A-g | Arrow |
| 0 | 12 | 11 | 0 | 8 | 5 | 8 |
| 3 | 12 | 6 | 0 | 6 | 5 | 6 |
| 5 | 11 | 6 | 0 | 5 | 5 | 5 |
| 7 | 11 | 5 | 0 | 4 | 0 | 0 |
| 9 | 10 | 5 | 0 | 0 | 0 | 0 |

The data demonstrates a markedly enhanced anti-fungal activity (*C. albicans*) with the gentian violet treatments, as compared to the standard Arrow catheter.

EXAMPLE 11

Gentian violet bacterial inhibition using polyurethane catheters

Gentian violet was dissolved in water to achieve the five concentrations listed in Table 10 below. Polyurethane cath-

TABLE 8

Release of Gentian Violet into aqueous and alcohol solutions from catheters treated in 70% alcohol and 2% Gentian Violet for 7 days and in the following solutions for another 7 days

| First Treatment | Second treatment (days 8 to 14); continuous soaking in aqueous and alcohol solutions | | | | | | Continous soaking with LRS changes every 24 hrs | | | |
|---|---|---|---|---|---|---|---|---|---|---|
| (days 1 to 7) | Solution | Day 8 | Day 9 | Day 10 | Day 11 | Day 14 | Day 15 | Day 16 | Day 17 | Day 24 |
| 70% alcohol + 2% Gentian Violet | 20% Silver Nitrate in Water | 2+ | 2+ | 2+ | 2+ | 2+ | 3+ | 3+ | 1+ | 1+ |
| same | 20% Silver Nitrate in 70% alcohol | 4+ | 8+ | 8+ | 8+ | 10+ | NM | NM | NM | NM |
| same | Water | 2+ | 4+ | 4+ | 4+ | 4+ | 0+ | 1+ | 0+ | 1+ |
| same | 70% alcohol | 4+ | 8+ | 8+ | 8+ | 8+ | NM | NM | NM | NM |
| same | None | | | | | | 1+ | 2+ | 1+ | 1+ |

NM = non-measurable

EXAMPLE 10

Gentian violet treated vs. Arrow Catheter - Short Term Study

The present example demonstrates the bacterial inhibition provided by treatment of polyurethane with gentian violet. Three representative microorganisms, *C. albicans*, *E. coli* eters were exposed to the resulting gentian violet solutions at room temperature for seven days with occasional agitation, rinsed 10 times in water for injection, dried and gas sterilized. These procedures were carried out under a laminar flow hood using sterile instruments and glassware; the bioreactor, proposed for use in clinical studies, was not used due to the small size of treated tubing.

The specific bactericidal effects of these gentian violet-treated catheters were assessed by incubating their short segments in agar-poured plates inoculated with different pathogens. Following 48 hours incubation at 37° C. with the four microorganisms most frequently involved in catheter related sepsis - *Staphylococcus epidermidis*, *Staphylococcus aureus*, *Escherichia coli*, and *Candida albicans* - the plates were examined and the diameter of inhibition zone was determined. As illustrated in Table 10, the treated catheter segments exhibited consistent growth inhibition of three of the tested pathogens.

The inhibitory effects of various gentian violet concentrations were compared to identify the most effective concentration for optimal absorption to polyurethane material and, consequently, the best bactericidal activity. The inhibitory effects against the three gentian violet-sensitive organisms (*Candida albicans*, *Staphylococcus aureus*, *Staphylococcus epidermidis*) increased with the increased content of the dye in the first three tested solutions (0.01–1%). Further concentration increases (2% and 4%) did not result in any further enhancement of the bacteriostatic activity, probably due to the fact that the 1% gentian violet solution appeared to reach the point of saturation.

TABLE 10

Bacteriostasis effects of various concentrations of gentian violet treatment of polyurethane

| | Inhibition Zone (in mm) | | | |
|---|---|---|---|---|
| | C. albicans | E. coli | S. aureus | S. epidermidis |
| 0.01% GV | 11 | — | 8 | 7 |
| | 12 | 0 | 8 | 7 |
| | 7 | | 2 | 4 |
| | 11 | | 6 | 8 |
| Mean | 10 | | 6 | 7 |
| 0.10% GV | 16 | — | 7 | 11 |
| | 17 | 0 | 10 | 12 |
| | | | 5 | 8 |
| | 13 | | 6 | 8 |
| Mean | 15 | | 9 | 12 |
| 1.00% GV | 19 | — | 11 | 13 |

TABLE 10-continued

Bacteriostasis effects of various concentrations of gentian violet treatment of polyurethane

| | Inhibition Zone (in mm) | | | |
|---|---|---|---|---|
| | C. albicans | E. coli | S. aureus | S. epidermidis |
| | 17 | 0 | 10 | 12 |
| | 17 | | 8 | 10 |
| | 18 | | 8 | 11 |
| Mean | 18 | | 9 | 12 |
| 2.00% GV | 6 | 0 | 0 | 5 |
| | 18 | | 8 | 11 |
| | 20 | | 9 | 11 |
| Mean | 15 | | 9 | 9 |
| 4.00% GV | 6 | 0 | 0 | 5 |
| | 18 | | 8 | 11 |
| | 20 | | 9 | 11 |
| Mean | 15 | | 9 | 9 |

EXAMPLE 12

The extent of bacterial inhibition by catheters, impregnated with gentian violet solutions containing various concentrations of alcohol, was assessed and compared with matching data obtained from the same treatment in aqueous solutions.

The results from this study are below in Table 11. The data confirmed the results of previous tests estimating the amount of gentian violet absorbed by polyurethane from its color. The increase of alcohol content in the impregnating solutions did not enhance the amounts of dye retained in the catheters, and subsequently, their bactericidal potency. Despite its improvement of the dye solubility, higher alcohol concentrations demonstrated a tendency to lower the inhibition zones generated by all the catheters, irrespective of the gentian violet concentration in the treatment solutions. However, most of the differences between the catheters impregnated with solutions with or without alcohol were insignificant and in no instance did the alcohol abolish the bacteriostatic effects.

TABLE 11

The effects of gentian violet and ethanol contents in the treatment solution on the bacteriocidal activity of treated polyurethane catheters

| | 5% Alcohol | | | 25% Alcohol | | | 50% Alcohol | | | 70% Alcohol | | | 95% Alcohol | | |
|---|---|---|---|---|---|---|---|---|---|---|---|---|---|---|---|
| 0.01% GV | 9 | 5 | 8 | 10 | 3 | 7 | 7 | 3 | 4 | 14 | 8 | 10 | 5 | 3 | 3 |
| 0.10% GV | 16 | 8 | 11 | 15 | 7 | 9 | | | | 7 | 3 | 6 | — | — | — |
| 1.00% GV | 20 | 10 | 13 | 20 | 11 | 13 | — | — | — | 17 | 9 | 12 | — | — | — |

C. a. = *Candida albicans*
S. e. = *Staphylococcus epdermides*
S. a. = *Staphylococcus aureus*

EXAMPLE 13

Long Term Bacterial Inhibition With Low Concentrations of Gentian Violet

In this study, long term bacterial inhibition of low amounts of gentian violet after long-term dry storage was demonstrated.

Catheters 10 cm in length were soaked in water containing 0.01% gentian violet for seven days at room temperature. These were rinsed in water 10 times; after this wash the water presented no coloration. The catheters were then dried and cut into 2mm segments, gas sterilized and stored. Six segments were removed at monthly intervals for a year and tested in duplicate for bacterial inhibition. The results in Table 12 below demonstrate that even the low concentrations of gentian violet may provide extended anti-bacterial and anti-fungal activity during storage for up to one year.

TABLE 12

Long-term Bacteriocidal Effects of Gentian Violet-treated Polyurethane Catheters
Zone Inhibition - Abbott Laboratories Catheter (Diameter in mm)

| Time (Month) | Escherichia coli | Staphylococcus epidermidis | Staphylococcus aureus | Candida albicans |
|---|---|---|---|---|
| 0 | 0 | 5 | 9 | 16 |
| 1 | 0 | 5 | 9 | 16 |
| 2 | 0 | 7 | 6 | 13 |
| 3 | 0 | 7 | 6 | 13 |
| 4 | 0 | 5 | 4 | 10 |
| 5 | 0 | 6 | 4 | 8 |
| 6 | 0 | 6 | 5 | 8 |
| 7 | 0 | 6 | 5 | 10 |
| 8 | 0 | 7 | 5 | 12 |
| 9 | 0 | 6 | 5 | 9 |
| 10 | 0 | 7 | 6 | 10 |
| 11 | 0 | 6 | 5 | 8 |
| 12 | 0 | 6 | 7 | 8 |

EXAMPLE 14

In Vivo Studies with Gentian Violet-treated Polyurethane to Assess Release of Gentian Violet into Surrounding Tissues Polyurethane catheter segments treated with 0.01, 0.1 and 1% gentian violet were implanted both intracutaneously (open wound) and subcutaneously (closed pockets) in a rat. Non-treated catheter segments were implanted in the same manner. Each implant site was seeded with two drops of Staphylococcus epidermidis culture, to simulate clinical conditions in presence of opportunistic organisms. Five days after the implants, the segments were removed and, following macroscopic inspection, the surrounding tissues were excised and submitted for histologic examination.

There were no obvious macroscopic differences between any of the treated or the control catheters implanted intradermally in the surrounding tissue or in the developed scabs. In contrast, subcutaneous implantation of treated segments resulted in some tissue staining and induced angiogenesis, both of these phenomena increasing with the increased concentration of the dye.

EXAMPLE 15

Addition of Silver Nitrate to Gentian Violet Treatment to Increase the Anti-bacterial Activity To increase the bacteriostatic spectrum to include gram-negative microorganisms, the addition of silver nitrate to the catheter treatment was tested. Since alcohol-based solutions facilitated silver nitrate incorporation into silastic material, the effects of varying solvent contents on polyurethane absorption were examined. The methods of catheter treatments with solutions specified below were similar to those previously described for gentian violet. Following the treatments, one week of continuous soaking in LRS following the treatments was again used to estimate the remaining efficiency of catheters at the end of theoretical maximal implantation time in situ. There were no bacteriostatic effects noted following one week of catheter immersion in alcohol solution only, irrespective of its concentrations. Similarly to the silastic material, the highest bactericidal effect after addition of silver nitrate were noted in solvents with alcohol contents of 70%. (Table 13).

TABLE 13

The bacteriostatic effects of $AgNO_3$ in various solvents, as represented in zone inhibition (in mm) of four pathogens tested

| | | Zone Inhibition (mm in diameter) | | | |
|---|---|---|---|---|---|
| First Treatment (day 1–7) | Second Treatment (day 7–14) | Candida ablicans | Escherichia coli | Staphylococcus aureus | Staphyloccus epidermidis |
| 25% ethanol | LRS | 0 | 0 | 0 | 0 |
| 70% ethanol | LRS | 0 | 0 | 0 | 0 |
| Silver Nitrate 20% in Water | LRS | 8 | 0 | 6 | 5 |
| Silver Nitrate 20% in 25% ethanol | LRS | 10 | 0 | 6 | 6 |
| Silver Nitrate 20% in 70% ethanol | LRS | 12 | 4 | 8 | 7 |
| Silver Nitrate 20% in Water | 0.01 Gentian Violet in Water | 12 | 0 | 8 | 11 |
| Silver Nitrate 20% in 70% ethanol | 0.01% Gentian Violet in Water | 12 | 4 | 8 | 12 |

EXAMPLE 16

Combined Treatment of Silver Nitrate and Gentian Violet

This study is provided to demonstrate the bacterial inhibition provided by treatment of a catheter surface first with gentian violet suspended in water, followed by a silver nitrate in alcohol treatment (70% alcohol).

The effectiveness of concomitant vs. consecutive modes of treatments with gentian violet and silver nitrate were considered in further studies determining again the inhibition zones of the four most common pathogens involved in catheter septic complications (*Staphylococcus epidermidis, Staphylococcus aureus, Escherichia coli,* and *Candida albicans*). In comparing the two possible variations of consecutive treatments with the antiseptic agents, the use of silver nitrate preceding the gentian violet impregnation consistently presented slightly larger inhibition zones than the opposite approach. The representative averages of data on bactericidal effects, comparing the consecutive and the simultaneous antiseptic use, and listed in Table 14, demonstrated virtually equal inhibition of all the tested pathogens following both modes of the treatment.

TABLE 14

Bacteriostasis effect of combined $AgNO_3$ and gentian violet treatment of polyurethane catheters

| First Treatment (days 1–7) | Second Treatment (days 7–14) | LRS soak (day 7–14) | Zone Inhibition (mm in diameter) | | | |
|---|---|---|---|---|---|---|
| | | | *Candida albicans* | *Escherichia coli* | *Staphylococcus aureus* | *Staphylococcus epidermidis* |
| Silver Nitrate 20% in 70% ethanol | 0.01% Gentian Violet in Water | Yes | 11 | 5 | 9 | 9 |
| Silver Nitrate 20% in 70% ethanol | 0.1% Gentian Violet in Water | Yes | 13 | 5 | 9 | 9 |
| Silver Nitrate 20% in 70% ethanol | 1.0 Gentian Violet in Water | Yes | 13 | 4 | 10 | 10 |
| Silver Nitrate 20% and 0.01% Gentian Violet in 70% ethanol | LRS soak | No | 9 | 5 | 10 | 8 |
| Silver Nitrate 20% and 0.1% Gentian Violet in 70% ethanol | LRS soak | No | 12 | 5 | 10 | 9 |
| Silver Nitrate 20% and 1.0% Gentian Violet in 70% ethanol | LRS soak | No | 16 | 5 | 12 | 14 |

(All of the presented data are average results from several (2 to 4) separate studies)

EXAMPLE 17

Determination of gentian violet content in polyurethane

The present example demonstrates the gentian violet contents in polyurethane catheters following the treatment with solutions of concentrations specified below. The catheters were treated, rinsed and soaked in LRS in the same manner as previously described.

Determination of gentian violet content in the catheters:

Preweighted segments of treated catheters were suspended in 2 ml of 70% alcohol at temperature of 65° C. for 90 minutes to elute all the absorbed dye. The concentration of gentian violet in the eluent was determined spectrophotometrically at a wave length of 591 nanometers (Beckman Spectrophotometer Model DU60) and recalculated for the segments weight. Table 15 presents results from this study.

TABLE 15

Gentian Violet concentration in polyurethane tubing

| Gentian Violet treatment solution (%) | Weight (g) | Gentian Violet released (µg) | Gentian Violet/Polyurethane (µg/g) | µg/mm² of surface | µg/cm² of surface |
|---|---|---|---|---|---|
| 0.01 | 0.14098 | 32.3 | 229 | 0.105 | 10.509 |
| 0.1 | 0.13725 | 46.2 | 337 | 0.155 | 15.467 |
| 1.0 | 0.13928 | 86.1 | 618 | 0.284 | 28.365 |
| 2.0 | 0.14354 | 105.7 | 736 | 0.338 | 33.780 | a. 10 mm segment = 0.346 g
b. 1 g = 298 mm
c. Outside diameter of segments = 2.4 mm
d. Outside circumference of segments = 7.539 mm
e. Surface of 1 g = 2.179 mm² = 21.79 cm²

EXAMPLE 18

Determination of silver nitrate content in polyurethane

The exact manner of the catheter treatments was described above and the measurements of resulting silver nitrate incorporation in the catheters were performed as follows: the treated segments were solubilized using microwave assisted nitric acid digestion and silver content in the digests was measured using inductively coupled plasma atomic emission spectroscopy at a wavelength of 328 nm (detection limits 7µg/L).

The highest incorporation of silver (>7,000 µg/gm) has resulted from treatments using 70% alcohol as the solvent. The high silver content coincided in all catheters with the most effective inhibition of gram-negative organisms growth. (Table 16).

TABLE 16

Silver content and bacteriocidal activity of AgNO$_3$-treated polyurethane catheters with or without gentian violet

| First Treatment (days 1–7) | Second Treatment (days 7–14) | LRS soak (days 7–14) | Zone Inhibition (mm in diameter) | | | | Ag content in polyurethane atheters | | |
|---|---|---|---|---|---|---|---|---|---|
| | | | Candida albicans | Escherichia coli | Staphylococcus aureus | Staphylococcus epidermidis | (µg/g) | (µg/mm2) | (µg/cm2) |
| Silver Nitrate 20% in Water | 0.01% Gentian Violet in Water | YeS | 15 | 0 | 9 | 11 | 1060 | 0.417 | 41.749 |
| Silver Nitrate 20% in 70% ethanol | 0.1% Gentian Violet in Water | Yes | 16 | 4 | 10 | 13 | 7860 | 3.096 | 309,571 |
| Silver Nitrate 20% in 25% ethanol | LRS soak | No | 10 | 0 | 6 | 6 | 1540 | 0.607 | 60.654 |
| Silver Nitrate 20% in 70% ethanol | LRS soak | No | 12 | 4 | 8 | 7 | 16500 | 6,499 | 649,862 |
| Silver Nitrate Gentian Violet in 25% ethanol | LRS soak | No | 12 | 0 | 7 | 9 | 480 | 0.189 | 18.905 |
| Silver Nitrate 20% and 1.0% Gentian Violet in 70% ethanol | LRS soak | no | 19 | 5 | 12 | 14 | 16100 | 6.341 | 634.108 |

EXAMPLE 19

Gentian violet and silver nitrate treated polyurethane catheters vs. Arrow catheter-short term study Bactericidal effects of polyurethane treated with silver nitrate and gentian violet were compared with those of commercially available Arrowgard™ Blue Line central venous catheters. Segments of all catheters were again embedded in poured agar plates containing one of four common catheter pathogens, as outlined herein. The results, presented in Table 17 were indicative of stronger inhibition by gentian violet-silver nitrate treatment of *Candida albicans Staphylococcus epidermis* and *Staphylococcus aureus* with slightly lower activity against *Escherichia coli*. Considering the preponderance of the former two pathogens in septic complications of immunosuppressed patients (as burns or AIDS), the proposed treatment may provide an optimal prophylaxis for the most severely ill in the future.

7. Docampo, et al. (1990), "The Metabolism and Mode of Action of Gentian Violet," Drug Metabolism Reviews, 22 (2&3), 161–178
8. Wilson, C. B., "More on Thrush and the Use of Gentian Violet," J. Hum. Lact. 7(2):58 (1991)
9. Nyst, et al., (1992) "Gentian Violet, Ketoconazole and Nystatin in Oropharyngeal and Esophageal Candiadiasis in Zairian AIDS Patients," Ann. Soc. Belg. Med. Trop., 72(1):45–52
10. Luquetti, A. O., (1990) "Risk of Cancer Development in Recipients of Gentian Violet-Treated Blood," Rev. Soc. Bras. Med. Trop. 23(4):237–238
11. Utter, A. R., (1990) "Gentian Violet Treatment For Thrush, Can Its Use Cause Breastfeeding Problems?" J. Hum. Lact. 6(4):178–180
12. U.S. Pat No. 4,642,104, Sakamoto, et al. (1987)
13. European Patent Application No. 8–510755984, Haynes, et al. (1986)
14. Solomon et al., (1987), J. Controlled Release, 6:343–52.
15. U.S. Pat. No. 4,442,133

TABLE 17

Comparison of bacteriocidal effects of Gentian Violet and AgNO3-treated catheters with those of Arrowgard ™ Blue Line

| First Treatment (days 1–7) | Second Treatment (days 7–14) | LRS soak (days 14–21) | Zone Inhibition (mm in diameter) | | | |
|---|---|---|---|---|---|---|
| | | | *Candida albicans* | *Escherichia coli* | *Staphylococcus aureus* | *Staphyloccus epidermidis* |
| Silver Nitrate 20% in 70% ethanol | 0.01% Gentian Violet in Water | yes | 10 | 5 | 9 | 8 |
| Silver Nitrate 20% in 70% ethanol | 0.1% Gentian Violet in Water | yes | 12 | 4 | 8 | 9 |
| Silver Nitrate 20% in 70% ethanol | 1.0% Gentian Violet in Water | yes | 11 | 4 | 10 | 9 |
| Silver Nitrate 20% and 0.01 Gentian Violet in 70% ethanol | LRS soak | no | 7 | 5 | 9 | 7 |
| Silver Nitrate 20% and 0.1% Gentian Violet in 70% ethanol | LRS soak | no | 11 | 5 | 9 | 7 |
| Silver Nitrate 20% and 1.0% Gentian Violet in 70% ethanol | LRS soak | no | 18 | 5 | 11 | 14 |
| Arrow Catheter | LRS soak | no | 9 | 7 | 7 | 10 |

REFERENCES

The following references, to the extent that they provide exemplary procedural or other details supplementary to those set forth herein, are specifically incorporated herein by reference.

1. U.S. Pat. No. 4,592,920, Murtfeldt (1986)
2. European Patent Application No. 0206024 —Becton Dickinson
3. Illner, et al. (1989), "Use of Topical Antiseptic in Prophylaxis of Catheter—Related Septic Complications," Surgery, Gynecology & Obstetrics, 168:481–490.
4. Bhatnagar et al., (1993) Indian Journal of Medical Research, 97:206–208
5. Drinkwater, P., (1990) "Gentian Violet—Is It Safe?" (editorial) Aust. N. 2. J. Obstet. Gynaecol. 30(1):665–656
6. Amato, et al., (1990) "Risk of Developing Cancer in Recipients of Gentian Violet Blood, Validity of the Interview," Ref. Soc. Bras. Med. Trop. 23(1):53
16. Beam T. R. Jr., Goodman E. L., Farr B. M., Maki D. G., Mayhall C. G.: (1990) "preventing central venous catheter-relating complications." Infect. in Surg., 1–13.
17. Trooskin S. Z., Donetz A. P., Harvey R. A., Greco R. S.: (1985 "Prevention of catheter sepsis by antibiotic bonding." Surg., 97(5):547–551.
18. Bach A., et al: (1993) "Prevention of catheter-related infections by antiseptic bonding." J. of Surg. Res. (55), 640–646.
19. Benvenisty, Al, et al: (1988) "Control of prosthetic bacterial infection: Evaluation of an easily incorporated, tightly bound, silver antibiotic TFE; graft." J. of Surg. Res. (44) 1–7.
20. Jacobson, M. A., Gellerman H., Chambers H.: Staphylococcus aureus bacteremia nd recurrent Staphylococcal infection in patients with Acquired Immunodeficiency Syndrome and AIDS-related complex. Amer. J. Med. 85:172–176, 1988.

21. Murr, M. M., Rosenquist M. S., Lewis, II, R. W., Heinle, J. A., Kealey, G. P.: A prospective safety study of femoral vein versus nonfemoral vein catheterization in patients with burns. J. Burn Care & Rehab. 12(6): 576–578, 1991.

What is claimed is:

1. A medical device comprising silicone having a surface that includes an antimicrobially and antifungally effective amount of gentian violet of about 0.01% to about 0.05% by weight.

2. The medical device of claim 1 further defined as a catheter.

3. A medical device comprising silicone having a surface that includes an amount of gentian violet of about 0.01% to about 0.1% by weight, wherein said silicone further comprises an antimicrobially effective amount of silver nitrate.

4. The medical device of claim 3 wherein the amount of gentian violet is about 0.01% by weight.

5. The medical device of claim 3 wherein the amount of silver nitrate is about 0.1% by weight to about 2.0% by weight.

6. A medical device comprising polyurethane having a surface comprising an antimicrobially and antifungally effective amount of gentian violet of about 0.01% by weight to about 0.05% by weight.

7. The medical device of claim 6 wherein the amount of gentian violet is about 0.01% by weight.

8. The medical device of claim 6 further defined as catheter.

9. A medical device comprising polyurethane having a surface that includes an amount of gentian violet of about 0.01% to about 0.1% by weight, wherein said polyurethane is further defined as comprising an antimicrobially effective amount of silver nitrate.

10. The medical device of claim 9 wherein the amount of silver nitrate is about 0.1% by weight to about 2.0% by weight.

* * * * *